United States Patent
Ravi et al.

(10) Patent No.: US 9,346,744 B2
(45) Date of Patent: May 24, 2016

(54) PROCESS FOR THE PREPARATION OF LACOSAMIDE AND ITS NOVEL INTERMEDIATE

(71) Applicant: Davuluri Ramamohan Rao, Hyderabad (IN)

(72) Inventors: Ponnaiah Ravi, Madurai (IN); Vishal Rajput, Hyderabad (IN); Mailapalli Dhanunjaya, Srikakulam (IN); Bondada Anilkumar, Hyderabad (IN)

(73) Assignee: Davuluri Ramamohan Rao, Hyderabad (IN)

( * ) Notice: Subject to any disclaimer, the term of this patent is extended or adjusted under 35 U.S.C. 154(b) by 0 days.

(21) Appl. No.: 14/641,949

(22) Filed: Mar. 9, 2015

(65) Prior Publication Data

US 2016/0060210 A1    Mar. 3, 2016

(30) Foreign Application Priority Data

Aug. 28, 2014 (IN) ............................ 4228/CHE/2014

(51) Int. Cl.
| | |
|---|---|
| *C07C 231/08* | (2006.01) |
| *C07C 231/02* | (2006.01) |
| *C07C 231/12* | (2006.01) |
| *C07C 51/29* | (2006.01) |
| *C07C 235/06* | (2006.01) |
| *C07C 247/12* | (2006.01) |
| *C07C 51/27* | (2006.01) |

(52) U.S. Cl.
CPC ............... *C07C 231/08* (2013.01); *C07C 51/27* (2013.01); *C07C 51/29* (2013.01); *C07C 231/02* (2013.01); *C07C 231/12* (2013.01); *C07C 235/06* (2013.01); *C07C 247/12* (2013.01)

(58) Field of Classification Search
CPC .. C07C 231/08; C07C 231/12; C07C 231/02; C07C 51/29; C07C 247/12; C07C 235/06
See application file for complete search history.

(56) References Cited

U.S. PATENT DOCUMENTS

2007/0155926 A1 *  7/2007  Matyjaszewski ..... C08F 212/08
                                                                526/303.1

FOREIGN PATENT DOCUMENTS

JP          57024362       *   2/1982

OTHER PUBLICATIONS

Muthukrishnan et al, Tetrahedron Assymetry, 22(12), 1353-1357, 2011.*
Yasumoto et al, Journal of Fluorine Chemistry, 131(2), 266-269, 2010.*

* cited by examiner

*Primary Examiner* — Shailendra Kumar
(74) *Attorney, Agent, or Firm* — Ling Wu; Stephen Yang; Ling and Yang Intellectual Property

(57) ABSTRACT

An improved, cost effective process for the preparation of Lacosamide is disclosed. A novel intermediate of formula (IV) and a process for preparation of the novel intermediate is also disclosed.

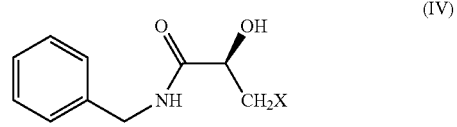

wherein, X is halogen.

23 Claims, No Drawings

PROCESS FOR THE PREPARATION OF LACOSAMIDE AND ITS NOVEL INTERMEDIATE

FIELD OF THE INVENTION

The invention relates to an improved process for the preparation of Lacosamide having formula (I).

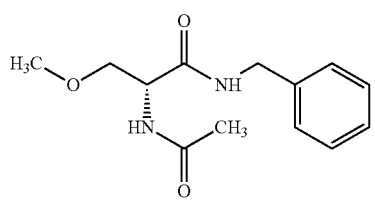

(I)

The invention also relates to a novel intermediate of formula (IV) for the synthesis of Lacosamide (I), and process of preparation of formula (III) and formula (IV)

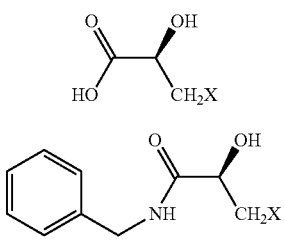

(III)

(IV)

wherein, X is halogen.

BACKGROUND OF THE INVENTION

Lacosamide [(R)-2-acetamido-N-benzyl-3-methoxypropionamide] of formula (I) is disclosed in U.S. RE 38,551. It shows effects in the treatment of pain, epilepsy, fibromyalgia syndrome, osteoarthritis and migraine.

The process for preparation of Lacosamide of formula (I) is disclosed in U.S. RE 38,551, WO 2006037574 and WO 2010052011.

The processes disclosed in these references are having following disadvantages:
a) Use of very expensive and hazardous reagents like silver oxide or butyllithium results in partial racemization which reduces the yield.
b) Purification with column chromatography techniques which is very difficult in commercial scale.
c) Use of expensive starting material.
d) Late stage optical resolution to afford high optical purity of Lacosamide.

In view of the preparation methods available for Lacosamide, there is a need for simple and cost effective process for the preparation of Lacosamide with high optical purity avoiding the use of expensive starting material and late stage optical resolution.

OBJECTS OF THE INVENTION

Primary object of the invention is to provide an improved process for the preparation of Lacosamide.

Another object of the invention is to provide a simple and cost effective process for the preparation of Lacosamide with high optical purity.

Another object of the invention is to provide an industrially viable process for the preparation of Lacosamide avoiding expensive materials and late stage optical resolution.

A further object of the invention is to provide novel intermediates for the synthesis of Lacosamide.

SUMMARY OF THE INVENTION

Accordingly, in one aspect, the invention provides a novel process for the preparation of a compound of formula (III)

(III)

wherein, X is halogen
which comprises:
regioselective ring opening of a compound of formula (II)

(II)

wherein, X is halogen,
in the presence of water, followed by oxidation with oxidising agent to obtain compound of formula (III).

In another aspect, the invention provides a novel intermediate of formula (IV) which is useful in the preparation of Lacosamide of formula (I)

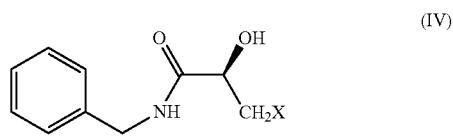

(IV)

wherein X is halogen.

In another aspect, the invention provides a process for preparation of optically pure or optically enriched novel intermediate of formula (IV)

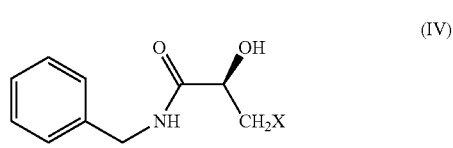

(IV)

wherein, X is halogen
which comprises:
Step 1: regioselective ring opening of compound of formula (II);

(II)

[structure: epoxide with CH₂X]

in presence of water, followed by oxidation with oxidising agent to obtain compound of formula (III);

(III)

[structure: HO-C(=O)-CH(OH)-CH₂X]

wherein, X is halogen;

Step 2: reaction of compound of formula (III) with benzyl amine in the presence of base and coupling agent to obtain formula (IV).

(IV)

[structure: benzyl-NH-C(=O)-CH(OH)-CH₂X]

In another aspect, the invention provides a process for the preparation of Lacosamide of formula (I), (I)

[structure of Lacosamide]

which comprises:

Step 1: regioselective ring opening of compound of formula (II)

(II)

[structure: epoxide with CH₂X]

wherein X is halogen,
in the presence of water, followed by oxidation with oxidising agent to obtain compound of formula (III);

(III)

[structure: HO-C(=O)-CH(OH)-CH₂X]

Step 2: reaction of compound of formula (III) with benzyl amine in the presence of base and coupling agent to obtain formula (IV)

(IV)

[structure: benzyl-NH-C(=O)-CH(OH)-CH₂X]

Step 3: reaction of compound of formula (IV) with base in alcohol solvent to obtain a compound of formula (V);

(V)

[structure: benzyl-NH-C(=O)-CH(OH)-CH₂-O-CH₃]

Step 4: protection of hydroxyl group of compound of formula (V) with Tosyl chloride in presence of dimethyl amino pyridine, dichloromethane and triethyl amine at a temperature in the range of 20° C. to 40° C. to obtain compound of formula (VI);

(VI)

[structure: benzyl-NH-C(=O)-CH(OTs)-CH₂-O-CH₃]

Step 5: reaction of compound of formula (VI) with sodium azide in presence of dimethyl formamide and water at a temperature in the range of 60° C. to 80° C. for the period of 5 hours to 7 hours to obtain compound of formula (VII);

(VII)

[structure: benzyl-NH-C(=O)-CH(N₃)-CH₂-O-CH₃]

Step 6: reducing compound of formula (VII) with H₂ in presence of organic solvent and catalyst at a temperature in the range of 20° C. to 40° C. for the period of 2 hours to 4 hours to obtain compound of formula (VIII);

(VIII)

[structure: benzyl-NH-C(=O)-CH(NH₂)-CH₂-O-CH₃]

Step 7: acylation of compound of formula (VIII) with aceticanhydride in presence of dimethyl amino pyridine and anhydrous methylene dichloride at a temperature in the range of 25° C. to 35° C. for the period of 10 hours to 14 hours to obtain Lacosamide of formula (I).

In another aspect, the invention provides a process for the purification of the Lacosamide in ethyl acetate at a temperature in the range of 5° C. to 15° C. for the period of 15 minutes to 45 minutes to give the pure Lacosamide of formula (I).

In another aspect, the invention provides a process for the preparation of Lacosamide of formula (I) by using inexpensive, readily available and easy to handle reagents.

In another aspect, the invention provides process for the preparation of Lacosamide of formula (I) which can be readily scaled up and which does not require a special purification steps.

In yet another aspect, the present invention provides an improved process for the preparation of Lacosamide of formula (I) which is simple, convenient, economical and environment friendly.

DETAILED DESCRIPTION OF THE INVENTION

Accordingly, the present invention provides a process for the preparation of formula (III), Scheme-1 illustrates the process for the preparation of formula (III).

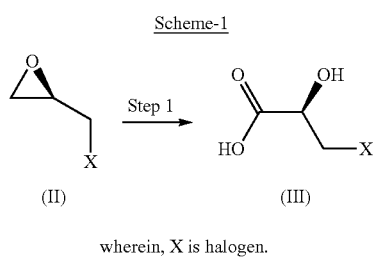

wherein, X is halogen.

This step comprises regioselective ring opening of formula (II) with water, followed by oxidation with suitable oxidizing agent to obtain compound of formula (III).

The oxidation agent used in the reaction is selected from nitric acid, sulfuric acid, hydrogen peroxide or potassium nitrate and preferably using nitric acid. The reaction temperature may range from 80° C. to 120° C. and preferably at a temperature in the range from 85° C. to 110° C. The duration of the reaction may range from 5 hours to 7 hours, preferably for a period of 6 hours.

In another aspect, the invention provides a novel intermediate of formula (IV), which is useful for the preparation of Lacosamide of formula (I).

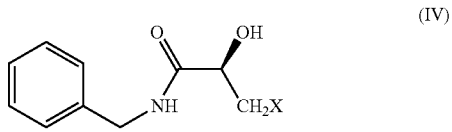

In yet another aspect, the invention provides a process for the preparation of novel intermediate of formula (IV), Scheme-2 illustrates the process for the preparation of formula (IV);

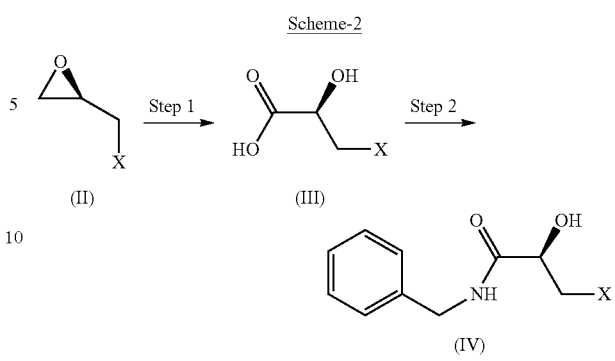

wherein, X is halogen.

The process of Scheme-2 comprises (i) regioselective ring opening of formula (II) with water, followed by oxidation with suitable oxidizing agent to obtain compound of formula (III);

The oxidation agent used in the reaction is selected from nitric acid, sulfuric acid, hydrogen peroxide or potassium nitrate and preferably using nitric acid. The reaction temperature may range from 80° C. to 120° C. and preferably at a temperature in the range from 85° C. to 110° C. The duration of the reaction may range from 5 hours to 7 hours, preferably for a period of 6 hours.

(ii) reacting the above obtained compound of formula (III) with benzyl amine in presence of base and coupling reagent to obtain compound of formula (IV).

The base employed in reaction can be selected from organic or inorganic base wherein the organic base is selected from the group comprising of isopropyl amine, diisopropyl amine, diisopropyl ethyl-amine, N-methyl morpholine, N-methyl piperidine, N-methyl piperazine, N-methyl pyridine or triethylamine. Inorganic base is selected from the group comprising of sodium, potassium, lithium, sodium carbonate, potassium carbonate, cesium carbonate, lithium carbonate, sodium bicarbonate, potassium bicarbonate, lithium bicarbonate, cesium bicarbonate, sodium hydroxide, calcium hydroxide or potassium hydroxide and preferably using N-methyl morpholine.

The coupling agent used in the reaction is selected from hydroxybenzotriazole and dicyclohexylcarbodiimide. The reaction temperature may range from 25° C. to 40° C. and preferably at a temperature in the range from 25° C. to 35° C. The duration of the reaction may range from 4 hours to 6 hours, preferably for a period of 5 hours.

According to another aspect of the invention, there is provided a process for the preparation of Lacosamide of formula (I).

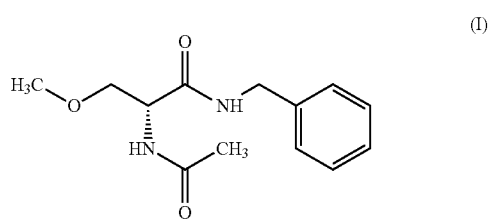 [SMILES: COC[C@@H](NC(C)=O)C(=O)NCc1ccccc1]

Scheme-3 illustrates the process for preparation of Lacosamide of formula (I);

Scheme-3

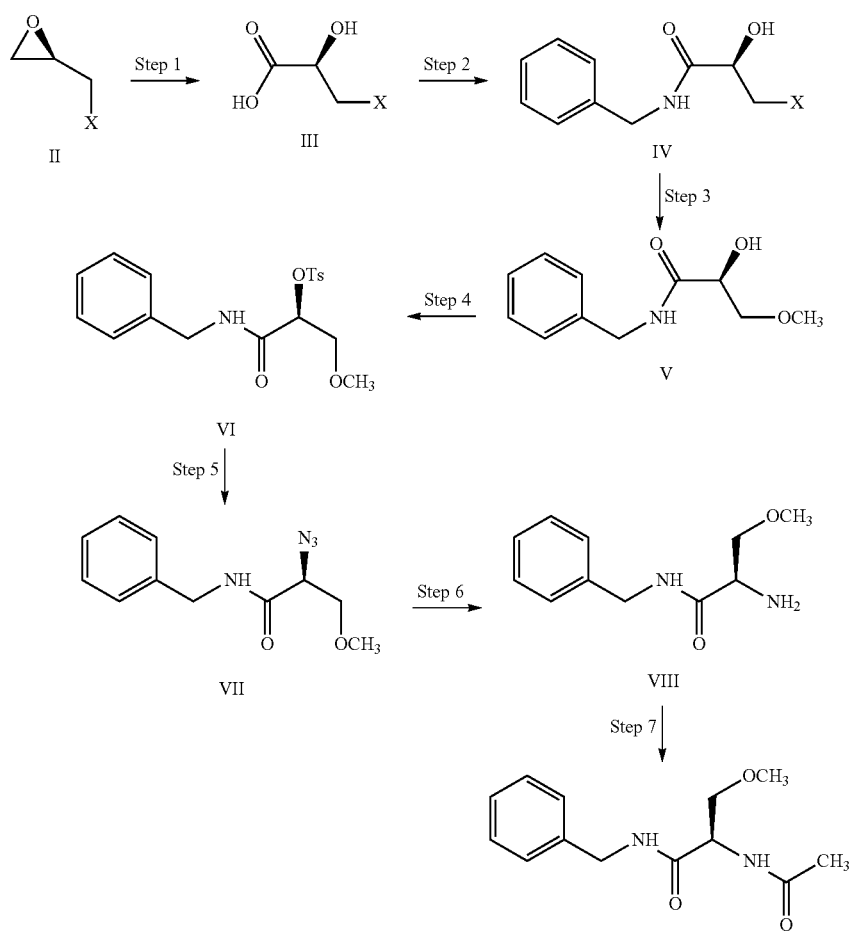

wherein, X is halogen; preferably chlorine.

The step-1 of scheme-3 comprises regioselective ring opening of formula (II) with water followed by oxidation with suitable oxidizing agent to obtain compound of formula (III).

The oxidation agent used in the reaction is selected from nitric acid, sulfuric acid, hydrogen peroxide or potassium nitrate and preferably using nitric acid. The reaction temperature may range from 80° C. to 120° C. and preferably at a temperature in the range from 85° C. to 110° C. The duration of the reaction may range from 5 hours to 7 hours, preferably for a period of 6 hours.

The step-2 of scheme-3 comprises reacting the above obtained compound of formula (III) with benzyl amine in presence of base and coupling reagent to obtain compound of formula (IV).

The base employed in reaction can be selected from organic or inorganic base wherein the organic base is selected from the group comprising of isopropyl amine, diisopropyl amine, diisopropyl ethyl-amine, N-methyl morpholine, N-methyl piperidine, N-methyl piperazine, N-methyl pyridine or triethylamine. Inorganic base is selected from the group comprising of sodium, potassium, lithium, sodium carbonate, potassium carbonate, cesium carbonate, lithium carbonate, sodium bicarbonate, potassium bicarbonate, lithium bicarbonate, cesium bicarbonate, sodium hydroxide, calcium hydroxide or potassium hydroxide and preferably using N-methyl morpholine. The coupling agents used in the reaction is selected from hydroxybenzotriazole and dicyclohexylcarbodiimide. The reaction temperature may range from 25° C. to 40° C. and preferably at a temperature in the range from 25° C. to 35° C. The duration of the reaction may range from 4 hours to 6 hours, preferably for a period of 5 hours.

The step-3 of scheme-3 comprises reaction of compound of formula (IV) with base in alcohol solvent to obtain a compound of formula (V).

The base used in this reaction is selected from methyl iodide, dimethyl sulphate, dimethyl carbonate, sodium methoxide or sodium ethoxide and preferably using sodium methoxide. The alcohol solvent is selected form methanol, ethanol, propanol, butanol, pentanol, and preferably methanol. The reaction temperature may range from −5° C. to 5° C. and preferably at a temperature in the range from 0° C. to 3° C. The duration of the reaction may range from 2 hours to 4 hours, preferably for a period of 3 hours.

The step-4 of scheme-3 comprises hydroxy protection of compound of formula (V) with tosyl chloride in presence of dimethyl amino pyridine, dichloromethane and triethyl amine to obtain compound of formula (VI). The reaction temperature may range from 20° C. to 40° C. and preferably at a temperature in the range from 25° C. to 35° C.

In Step 5 of the scheme-3, the above obtained compound of formula (VI) is reacted with sodium azide in the presence of dimethyl formamide and water to obtain compound of formula (VII). The reaction temperature may range from 60° C. to 80° C. and preferably at a temperature in the range from 65° C. to 75° C. The duration of the reaction may range from 5 hours to 7 hours, preferably for a period of 6 hours.

In Step 6 of this scheme, the above obtained compound of formula (VII) is reduced with $H_2$ in the presence of catalyst and organic solvent to obtain compound of formula (VIII). Catalyst used in the reaction can be selected from Pd/C, Pt/C, Raney Ni, Rh/C, Platinum oxide, $Pd(OH)_2$/C or Lithium aluminium hydride and preferably using palladium carbon. Organic solvent used in this reaction can be selected from alcohols or ketones and preferably methanol. The reaction temperature may range from 20° C. to 40° C. and preferably at a temperature in the range from 25° C. to 35° C. The duration of the reaction may range from 2 hours to 4 hours, preferably for a period of 3 hours.

In Step 7 of the scheme-3, the above obtained compound of formula (VIII) is acylated with acetic anhydride in presence of catalytic amount of dimethyl amino pyridine and anhydrous methylene dichloride to obtain Lacosamide of formula (I).

The reaction temperature may range from 20° C. to 40° C. and preferably at a temperature in the range from 25° C. to 35° C. The duration of the reaction may range from 10 hours to 14 hours, preferably for a period of 12 hours.

According to another aspect of the invention, there is provided a process for purification of Lacosamide compound of formula (I) by recrystallization in ethyl acetate. The reaction temperature may range from 5° C. to 15° C. and preferably at a temperature of 10° C. The duration of the reaction may range from 15 minutes to 45 minutes, preferably for a period of 30 minutes The following examples are provided to enable one skilled in the art to practice the invention and merely illustrate the process of the invention. However, it is not intended in any way to limit the scope of the present invention.

EXAMPLES

Example 1

Preparation of Compound of Formula (III)

To the round bottom flask having 100 mL of demineralised water (DM water) is charged compound of formula (II) (100 grams) at room temperature (RT) and subsequently reaction temperature is raised to 90° C., reaction mixture is allowed to stir at same temperature with vigorous stirring for 6 hours. Subsequently to the reaction mixture at 85° C. is added 65% aqueous nitric acid (250 mL) under controlled rate over 30 minutes in small aliquots and reaction mixture is heated to 110° C. The same temperature is maintained for additional 4 hours when thin layer chromatography (TLC), using 80% ethyl acetate (EtOAc)/hexane as mobile phase confirmed the full consumption of starting material and formation of slower moving spot. Reaction mixture is cooled to 10° C. and to reaction mixture is added 58 grams of sodium bicarbonate ($NaHCO_3$) while maintaining the same temperature. The product is extracted with ethyl acetate (EtOAc) (8×100 mL) and dried over magnesium sulphate. The solvent is then evaporated at room temperature (RT) and the temperature is raised to 60° C. towards the end of evaporation to remove residual nitric acid. The crude product solidified on standing at RT and is recrystallized from chloroform to yield 60 grams of colorless crystals of formula (III).

$^1$H-NMR (300 MHz, DMSO-$d_6$): d=12.89 (br s, 1H), 5.71 (br s, 1H), 4.31 (t, J=6.0 Hz, 1H), 3.78 (d, J=6.0 Hz, 1H);

MS(ESI): m/z=123.00 $[M-H]^+$.

Example 2

Preparation of Compound of Formula IV

To the cold reaction mixture of hydroxyl benzotriazole (HOBt) (68.28 grams) in dichloromethane (600 mL) is added to benzyl amine (60 mL) followed by N-methyl morpholine (63.48 mL) and dicyclohexylcarbodiimide (DCC) (104.28 grams) under nitrogen atmosphere. Subsequently, compound of formula (III) (60 grams) is added slowly to reaction mixture under nitrogen atmosphere over 30 minutes and reaction mass temperature is raised to RT and reaction mass is stirred for 5 hours at RT when TLC (50% EtOAc in n-hexane) showed complete consumption of staring material and formation of slower moving spot. Insoluble material is filtered off and resulted mother liquor is washed with 3N hydrochloric acid (HCl) (120 mL). The solvent is then evaporated at RT and the temperature is raised to 40° C. towards the end of evaporation. The crude product of formula (IV) (95 grams) is considered to subsequent stage without further purification.

$^1$H-NMR (300 MHz, DMSO-$d_6$): d=8.45 (t, J=6.0 Hz, 1H), 7.33-7.19 (m, 5H), 6.13 (d, J=6.0 Hz, 1H), 4.33-4.26 (m, 3H), 3.85-3.75 (m, 2H);

MS(ESI): m/z=212.05 $[M-H]^+$.

Example 3

Preparation of Compound of Formula (V)

To the reaction mixture of formula (IV) (90 grams) in methanol (55 mL) is charged 220 mL of 30% sodium methoxide in methanol at 0-3° C. under nitrogen atmosphere and the reaction is stirred for 3 hours at RT when TLC (50% EtOAc in n-hexane) showed complete consumption of staring material and formation of slower moving spot. To the reaction mixture is added 190 mL of 5N HCl and reaction mixture is stirred for 30 minutes at RT. The product is extracted with EtOAc (2×200 mL) and dried over magnesium sulphate. The solvent is then evaporated at RT and the temperature is raised to 60° C. towards the end of evaporation to remove residual solvent. The crude product compound of formula (V) (80 grams) is considered for subsequent stage without further purification.

$^1$H-NMR (300 MHz, DMSO-$d_6$): d=8.30 (t, J=6.0 Hz, 1H), 7.33-7.19 (m, 5H), 5.72 (d, J=6.0 Hz, 1H), 4.29 (d, J=6.0 Hz, 2H), 4.09-4.05 (m, 1H), 3.56-3.44 (m, 2H), 3.26 (s, 3H);

MS(ESI): m/z=210.13 $[M+H]^+$.

Example 4

Preparation of compound of formula VI

To the cold reaction mixture of formula (V) (80 grams) in 400 mL of dichloromethane is added to triethyl amine (64.09 mL) followed by tosyl chloride (87.3 grams) and dimethyl amino pyridine (0.05 equivalents, 2.3 grams) under $N_2$ gas atmosphere. Slowly reaction temperature is raised to 20° C. and reaction is stirred for 12 hours when TLC (50% EtOAc in n-hexane) showed complete consumption of starting material and formation of faster moving spot. To the reaction mixture is added 160 mL of water while stirring for additional 30 minutes. The organic layer is separated and dried over magnesium sulphate. The solvent is then evaporated at RT and the temperature is raised to 40° C. towards the end of evaporation to remove residual solvent. The crude product of formula (VI) is recrystallized with 240 mL of isopropanol at room temperature followed by cooling to 5° C. and obtained white solid is air dried for 3 hours. Isolated yield: 105 grams.

$^1$H-NMR (300 MHz, CDCl$_3$): d=7.79 (d, J=9.0 Hz, 2H), 7.75-7.24 (m, 5H), 7.21-7.19 (m, 2H), 6.72 (br s, 1H), 4.99 (dd, J=3.0 Hz, 3.0 Hz, 1H), 4.43-4.41 (m, 2H), 3.79 (dd, J=12.0 Hz, 3 Hz, 1H), 3.63 (dd, J=9.0 Hz, 3 Hz, 1H), 3.23 (s, 3H), 2.44 (s, 3H);

MS(ESI): m/z=364.14 [M+H]$^+$.

Example 5

Preparation of Compound of Formula VII

To a stirred solution of formula (VI) (55 grams) in dimethyl formamide and water (192 mL: 82 mL) at 70° C. under a N$_2$ atmosphere is added sodium azide (15 grams). The mixture is then allowed to stir at 70° C. for 6 hours, and then quenched with cool water (275 mL) at RT, the product is extracted with EtOAc (2×100 mL). The combined organic extracts are washed with cool water (200 mL), dried with sodium sulphate, and concentrated to give the crude product compound of formula (VII) (33 grams) as a pale yellow liquid. The crude is taken to subsequent step as such without any further purification.

$^1$H-NMR (300 MHz, CDCl$_3$): d=7.38-7.26 (m, 5H), 6.79 (br s, 1H), 4.47 (d, J=6.0 Hz, 2H), 4.25 (dd, J=6.0 Hz, 3.0 Hz, 1H), 3.94 (dd, J=12.0 Hz, 6.0 Hz, 1H), 3.77 (dd, J=9.0 Hz, 6.0 Hz, 1H), 3.43 (s, 3H);

MS(ESI): m/z=235.14 [M+H]$^+$.

Example 6

Preparation of Compound of Formula VIII

The obtained crude of formula (VII) (33 grams) is dissolved in methanol (150 mL) and to the reaction mixture in autoclave is added 5% palladium carbon (4.2 grams) at RT under nitrogen atmosphere. The reaction mixture is stirred for 3 hours at RT under 3 kg H$_2$ gas pressure. TLC (50% EtOAc in n-hexane) showed complete consumption of staring material and formation of slower moving spot. Filter the reaction mixture through celite pad and the celite pad is washed successively with hot methanol (30 mL). The solvent is then evaporated at RT and the temperature is raised to 50° C. towards the end of evaporation to remove residual solvent. The crude product of formula (VIII) (28 grams) is considered for subsequent stage without further purification.

$^1$H-NMR (300 MHz, DMSO-d$_6$): d=8.39 (s, 1H), 7.33-7.20 (m, 5H), 4.30 (dd, J=6.0 Hz, 3.0 Hz, 2H), 3.45-3.39 (m, 3H), 3.25 (s, 3H), 1.97 (s, 2H).

MS(ESI): m/z=209.17 [M+H]$^+$.

Example 7

Preparation of Compound of Formula I

To a stirred solution of formula (VIII) (27.7 grams) in anhydrous methylene dichloride (138 mL) is slowly added acetic anhydride (12.7 mL) and catalytic amount of dimethyl amino pyridine (0.5 grams). The resulting solution is stirred at RT for 12 hours. To the reaction mixture is added water (166 mL) and stirred for 15 minutes. The organic layer is successively washed with saturated sodium carbonate solution (83 mL). Organic layer is dried over sodium sulphate and solvent is evaporated to afford 31 grams of crude product of formula (I).

Example 8

Purification of Lacosamide

The above obtained crude 31 grams is taken in EtOAc (217 mL) and mixture is refluxed for 30 minutes. Subsequently, reaction mixture is allowed to cool at 10° C. while maintaining the stirring for additional 30 minutes. The obtained crystalline mass is filtered and solid cake is washed with chilled EtOAc (31 mL). Obtained solid is dried under vacuum to afford 25 grams of Lacosamide with high chiral purity.

$^1$H-NMR (300 MHz, DMSO-d$_6$): d=8.47 (t, J=6.0 Hz, 1H), 8.08 (d, J=6.0 Hz, 1H), 7.33-7.19 (m, 5H), 4.52-4.45 (m, 1H), 4.28 (d, J=6.0 Hz, 2H), 3.55-3.45 (m, 2H), 3.25 (s, 3H), 1.87 (s, 3H);

MS(ESI): m/z=251.15 [M+H]$^+$.

Advantages of the Invention

1. The process uses commercially available and less expensive starting material, namely (R)-Glycidyl chloride.
2. The present invention avoids cumbersome O-methylation step used in prior art (in earlier methods, this step involves expensive silver oxide, longer reaction period (3-4 days), and partial racemization).

We claim:
1. A process for the preparation of Lacosamide of formula (I)

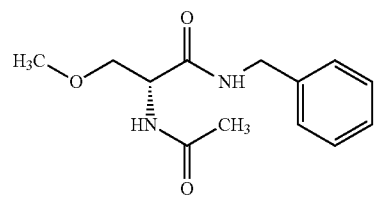

which comprises:
i). regioselective ring opening of compound of formula (II)

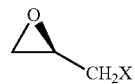

in presence of water, followed by oxidation with an oxidising agent to obtain compound of formula (III)

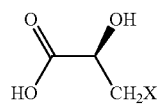

wherein, X is halogen;

ii). reaction of compound of formula (III) with benzyl amine in presence of a base and coupling agent to obtain a compound of formula (IV);

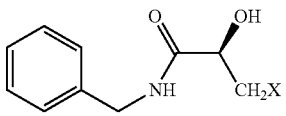

iii). reaction of compound of formula (IV) with a base in alcohol solvent to obtain a compound of formula (V);

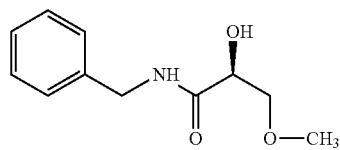

iv). protection of hydroxyl group of compound of formula (V) with Tosyl chloride in presence of dimethyl amino pyridine, dichloromethane and triethyl amine to obtain compound of formula (VI);

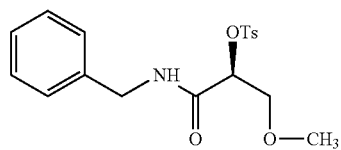

v). reacting compound of formula (VI) with sodium azide in presence of dimethyl formamide and water to obtain compound of formula (VII);

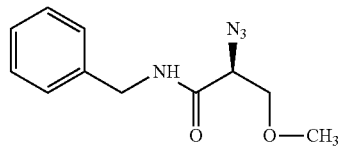

vi). reducing compound of formula (VII) with $H_2$ in the presence of organic solvent and catalyst to obtain compound of formula (VIII);

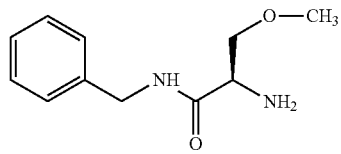

vii). acylation of compound of formula (VIII) with aceticanhydride in presence of dimethyl amino pyridine and anhydrous methylene dichloride to obtain Lacosamide of formula (I);

optionally, recrystalizing Lacosamide in ethyl acetate to give pure Lacosamide of formula (I).

2. The process as claimed in claim 1, wherein the oxidising agent is step (i) is nitric acid.

3. The process as claimed in claim 1, wherein the reaction of step (i) takes place at a temperature between 80° C. to 120° C.

4. The process as claimed in claim 1, wherein the coupling agent in Step (ii) is hydroxybenzotriazole and dicyclohexyl-carbodiimide.

5. The process as claimed in claim 1, wherein the base in Step (ii) is N-methyl morpholine.

6. The process as claimed in claim 1, wherein the base in Step (iii) is sodium methoxide.

7. The process as claimed in claim 1, wherein the alcohol solvent in Step (iii) is methanol.

8. The process as claimed in claim 1, wherein the reaction of step (iii) takes place at a temperature between 0° C. to 40° C.

9. The process as claimed in claim 1, wherein the reaction of step (iv) and step (vi) takes place at a temperature between 20° C. to 40° C.

10. The process as claimed in claim 1, wherein the reaction of step (v) takes place at a temperature between 60° C. to 80° C.

11. The process as claimed in claim 1, wherein the catalyst in step (vi) is palladium carbon.

12. The process as claimed in claim 1, wherein the solvent in step (vi) is methanol.

13. The process as claimed in claim 1, wherein the reaction of step (vii) takes place at a temperature between 25° C. to 35° C.

14. The process as claimed in claim 1, wherein the recrystallization of Lacosamide (I) is done at a temperature between 5° C. to 15° C.

15. A process for the preparation of a compound of formula (III)

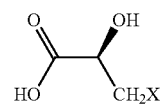

wherein, X is halogen,
which comprises regioselective ring opening of compound of formula (II)

with water, followed by oxidation with oxidising agent to obtain compound of formula (III)

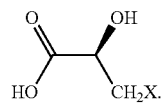

16. The process as claimed in claim 15, wherein the oxidizing agent is nitric acid.

17. The process as claimed in claim 15, wherein the reaction takes place at a temperature between 80° C. to 120° C.

18. A compound of formula (IV)

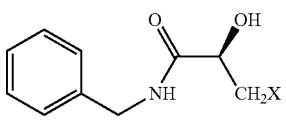

(IV)

wherein, X is halogen.

19. A process for the preparation of a compound of formula (IV)

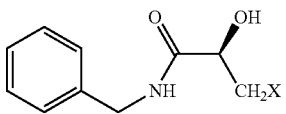

(IV)

wherein, X is halogen,
which comprises;
i). regioselective ring opening of formula (II)

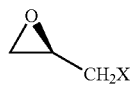

(II)

in the presence of water, followed by oxidation with oxidising agent to obtain compound of formula (III)

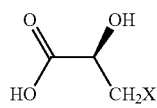

(III)

wherein, X is halogen;

ii). reaction of compound of formula (III) with benzyl amine in presence of base and coupling agent to obtain formula (IV)

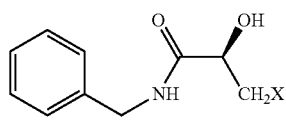

(IV)

20. The process as claimed in claim 19, wherein the oxidizing agent in step (i) is nitric acid.

21. The process as claimed in claim 19, wherein the reaction in step (i) takes place at a temperature between 80° C. to 120° C.

22. The process as claimed in claim 19, wherein the coupling agent in Step (ii) is hydroxybenzotriazole and dicyclohexylcarbodiimide.

23. The process as claimed in claim 19, wherein the base in Step (ii) is N-methyl morpholine.

* * * * *